US006527763B2

(12) United States Patent
Esch et al.

(10) Patent No.: US 6,527,763 B2
(45) Date of Patent: Mar. 4, 2003

(54) FLOW APPARATUS FOR THE DISRUPTION OF OCCLUSIONS

(75) Inventors: Victor C. Esch, San Francisco, CA (US); Quang Q. Tran, Fremont, CA (US); R. Rox Anderson, Lexington, MA (US)

(73) Assignee: Endovasix, Inc., Belmont, CA (US)

( * ) Notice: Subject to any disclaimer, the term of this patent is extended or adjusted under 35 U.S.C. 154(b) by 0 days.

(21) Appl. No.: 09/949,443

(22) Filed: Sep. 6, 2001

(65) Prior Publication Data

US 2002/0022827 A1 Feb. 21, 2002

Related U.S. Application Data

(60) Continuation of application No. 09/621,247, filed on Jul. 21, 2000, now abandoned, which is a division of application No. 09/120,598, filed on Jul. 22, 1998, now Pat. No. 6,139,543.

(51) Int. Cl.[7] ............................................... A61B 18/18
(52) U.S. Cl. ............................... 606/2; 606/8; 606/127
(58) Field of Search .............................. 606/2, 7, 8, 15, 606/127, 128

(56) References Cited

U.S. PATENT DOCUMENTS

| 4,587,972 A | 5/1986 | Morantte, Jr. |
| 4,685,458 A | 8/1987 | Leckrone |
| 4,739,768 A | 4/1988 | Engelson |
| 4,747,405 A | 5/1988 | Leckrone |
| 4,781,681 A | 11/1988 | Sharrow et al. |

(List continued on next page.)

FOREIGN PATENT DOCUMENTS

| DE | 3840126 A | 5/1990 |
| EP | 0571306 A | 11/1993 |
| WO | WO 9110403 A | 7/1991 |
| WO | WO9920189 | 4/1999 |
| WO | WO0003292 | 1/2000 |

OTHER PUBLICATIONS

Yuan, H. and Prosperetti, A (1997) "Gas–liquid Heat Transfer in a Bubble Collapsing Near a Wall," *Phys. Fluids* 9(1):127–142.

Brujan, E.A. et al. (1996) "Dynamics of Laser–Induced Cavitation Bubbles in Polymer Solutions," ACUSTICA *acta acustica 82*: 423–430.

Hao, Y. and Prosperetti, A. (1999) "The Dynamics of Vapor Bubbles in Acoustic Pressure Fields," *Physics of Fluids* 11(8):2008–2019.

Jun, Tomas K. and Kim, Chang–Jin (1996) "Microscale Pumping with traversing Bubbles in Microchannels," *Solid–State Sensor and Actuator Workshop*, Hilton Head, South Carolina pp. 144–147.

Oguz, H.N. and Prosperetti, A. (1998) "The Natural Frequency of Oscillation of Gas Bubbles in Tubes," *J. Acoust. Soc. Am.* 103:3301–3308.

Brookshier and J. M. Tarbell (1993) "Evaluation of a Transparant Blood Analog Fluid: Aqueous Xanthan Gum/Clycerin" *Biorheology* 30, 107–116.

Yuan, H. et al. (1999) "Growth and Collapse of a Vapor Bubble in a Small Tube," *International Journal of Heat and Mass Transfer* 42:3643–3657.

*Primary Examiner*—Roy D. Gibson
(74) *Attorney, Agent, or Firm*—Skjerven Morrill LLP; K. Alison De Runtz

(57) ABSTRACT

The invention encompasses methods and apparatus for pumping fluid from one location to another through the repetitive expansion and collapse of bubbles generated as a result of the absorption of repetitive pulses of radiation in a fluid. This pumping phenomenon can be used to aid removal of a total or partial occlusion in a body passage by emulsifying the occlusion with acoustic shock and pressure waves or by causing mechanically disrupting the occlusive material.

11 Claims, 12 Drawing Sheets

U.S. PATENT DOCUMENTS

| | | |
|---|---|---|
| 4,784,132 A | 11/1988 | Fox et al. |
| 4,878,492 A | 11/1989 | Sinofsky et al. |
| 5,026,367 A | 6/1991 | Leckrone et al. |
| 5,041,108 A | 8/1991 | Fox et al. |
| 5,041,121 A * | 8/1991 | Wondrazek et al. ......... 606/2.5 |
| 5,059,200 A | 10/1991 | Tulip |
| 5,085,659 A | 2/1992 | Rydell |
| 5,095,915 A | 3/1992 | Engelson |
| 5,109,859 A | 5/1992 | Jenkins |
| 5,116,227 A | 5/1992 | Levy |
| 5,207,988 A | 5/1993 | Lucas |
| 5,304,171 A | 4/1994 | Gregory et al. |
| 5,312,356 A | 5/1994 | Engelson et al. |
| 5,370,617 A | 12/1994 | Sahota |
| 5,397,301 A | 3/1995 | Pflueger et al. |
| 5,417,653 A | 5/1995 | Sabota et al. |
| 5,437,659 A | 8/1995 | Leckrone |
| 5,472,406 A * | 12/1995 | de la Torre et al. ............ 601/2 |
| 5,500,012 A | 3/1996 | Brucker et al. |
| 5,571,169 A | 11/1996 | Plaia et al. |
| 5,599,492 A | 2/1997 | Engelson |
| 5,649,923 A | 7/1997 | Gregory et al. |
| 5,662,590 A | 9/1997 | De La Torre et al. |
| 5,688,234 A | 11/1997 | Frisbie |
| 5,722,972 A | 3/1998 | Power et al. |
| 5,746,709 A | 5/1998 | Rom et al. |
| 5,776,127 A | 7/1998 | Anderson et al. |
| 5,817,144 A | 10/1998 | Gregory |
| 5,833,682 A | 11/1998 | Amplatz et al. |
| 5,944,687 A | 8/1999 | Bennett et al. |
| 5,964,751 A | 10/1999 | Amplatz et al. |
| 5,989,243 A | 11/1999 | Goldenberg |
| 6,022,309 A | 2/2000 | Celliers et al. |
| 6,024,738 A | 2/2000 | Daikuzono et al. |
| 6,033,371 A | 3/2000 | de la Torres et al. |
| 6,056,743 A | 5/2000 | Ellis et al. |
| 6,066,130 A | 5/2000 | Gregory et al. |
| 6,102,905 A | 8/2000 | Baxter et al. |
| 6,106,546 A | 8/2000 | Gregory |
| 6,139,543 A | 10/2000 | Esch et al. |
| 6,156,032 A | 12/2000 | Lennox |
| 6,200,307 B1 | 3/2001 | Kasinkas et al. |
| 6,210,400 B1 | 4/2001 | Herbert et al. |
| 6,295,990 B1 | 10/2001 | Lewis et al. |
| 6,156,029 A1 | 12/2001 | Mueller |
| 6,379,325 B1 * | 4/2002 | Benett et al. .................. 604/22 |

* cited by examiner

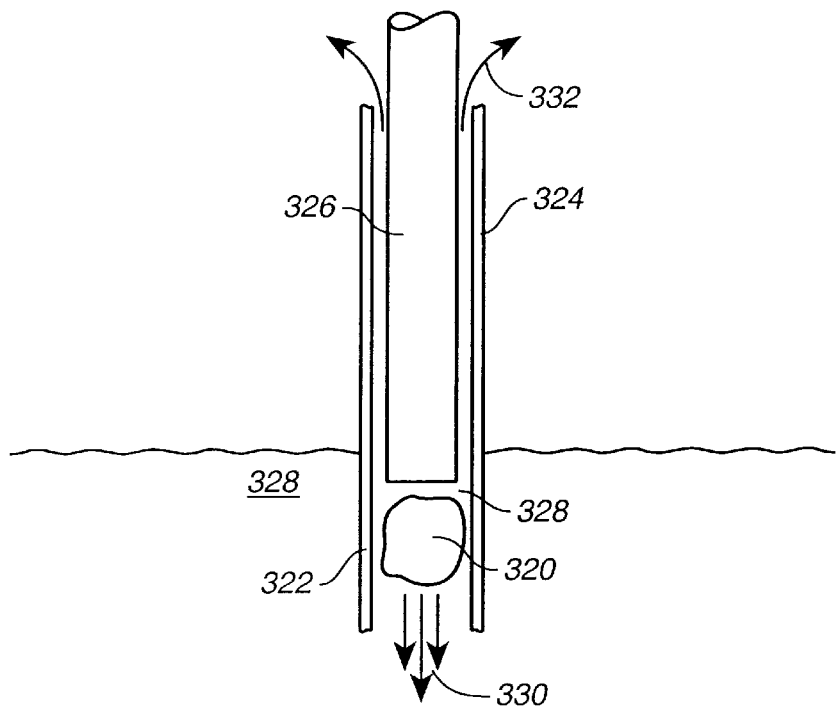
FIG._1 EXPANSION DIRECTION OF BUBBLE
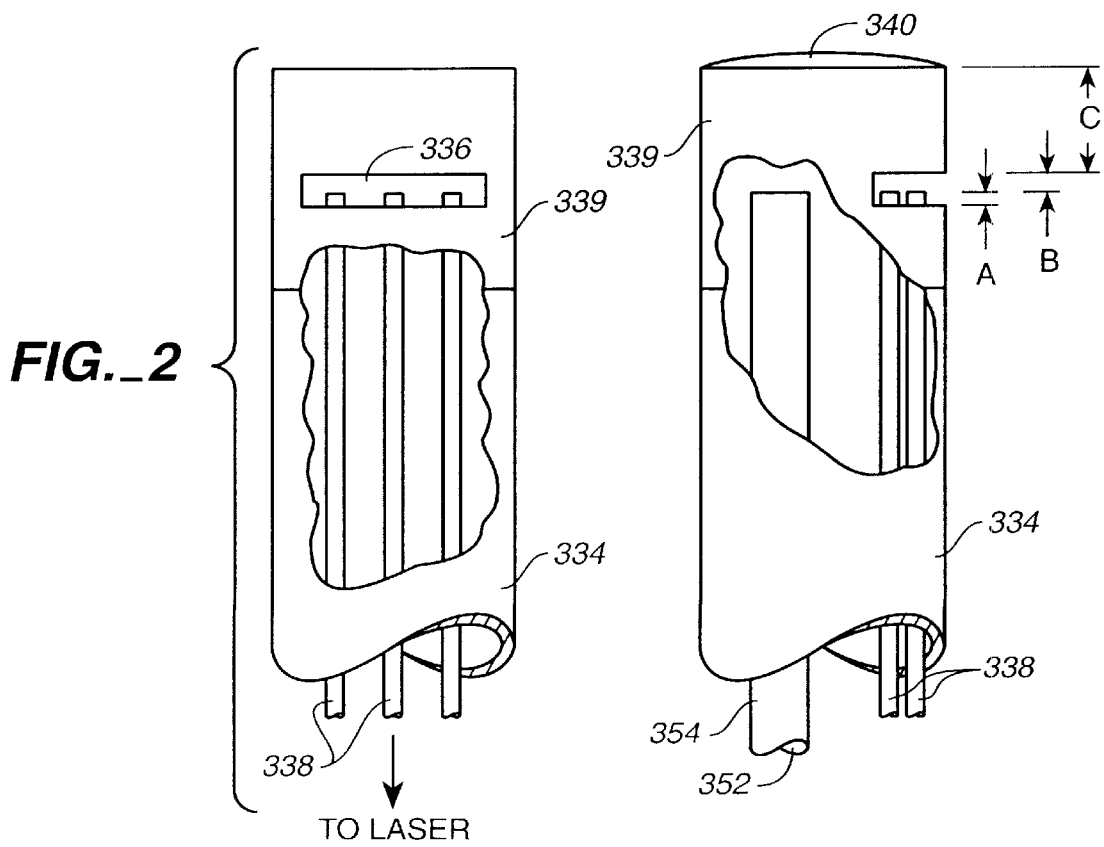
FIG._2

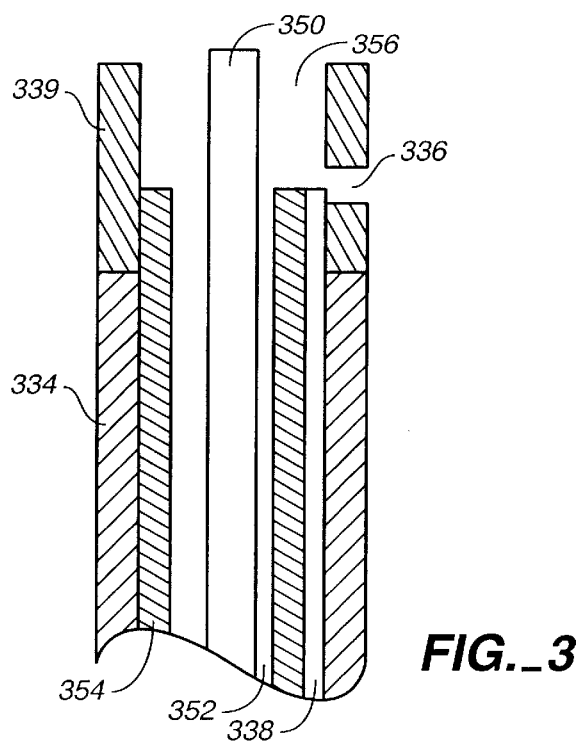
FIG._3
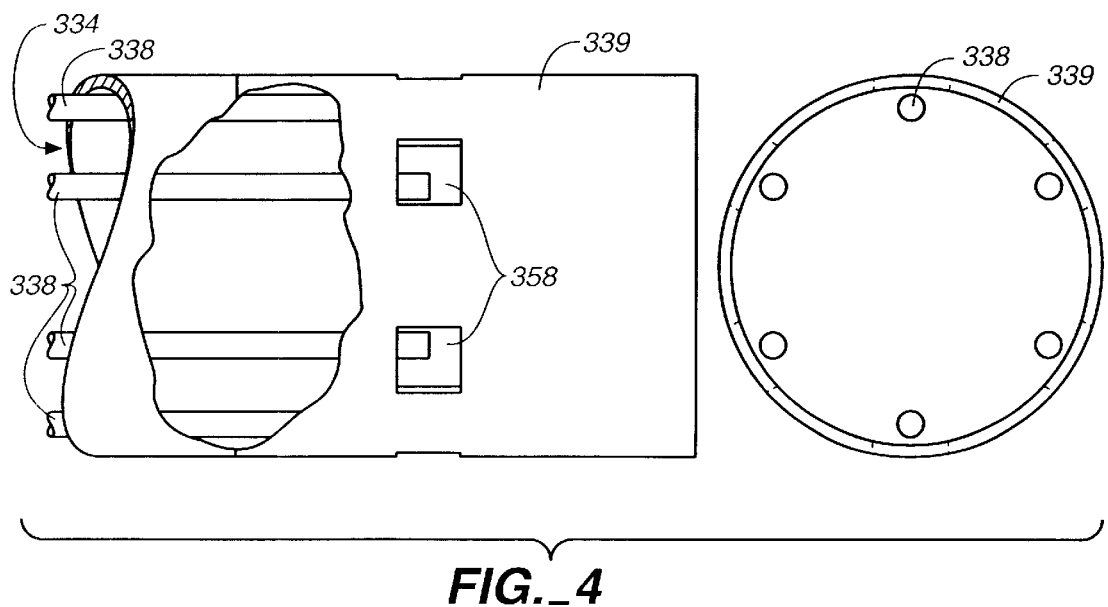
FIG._4

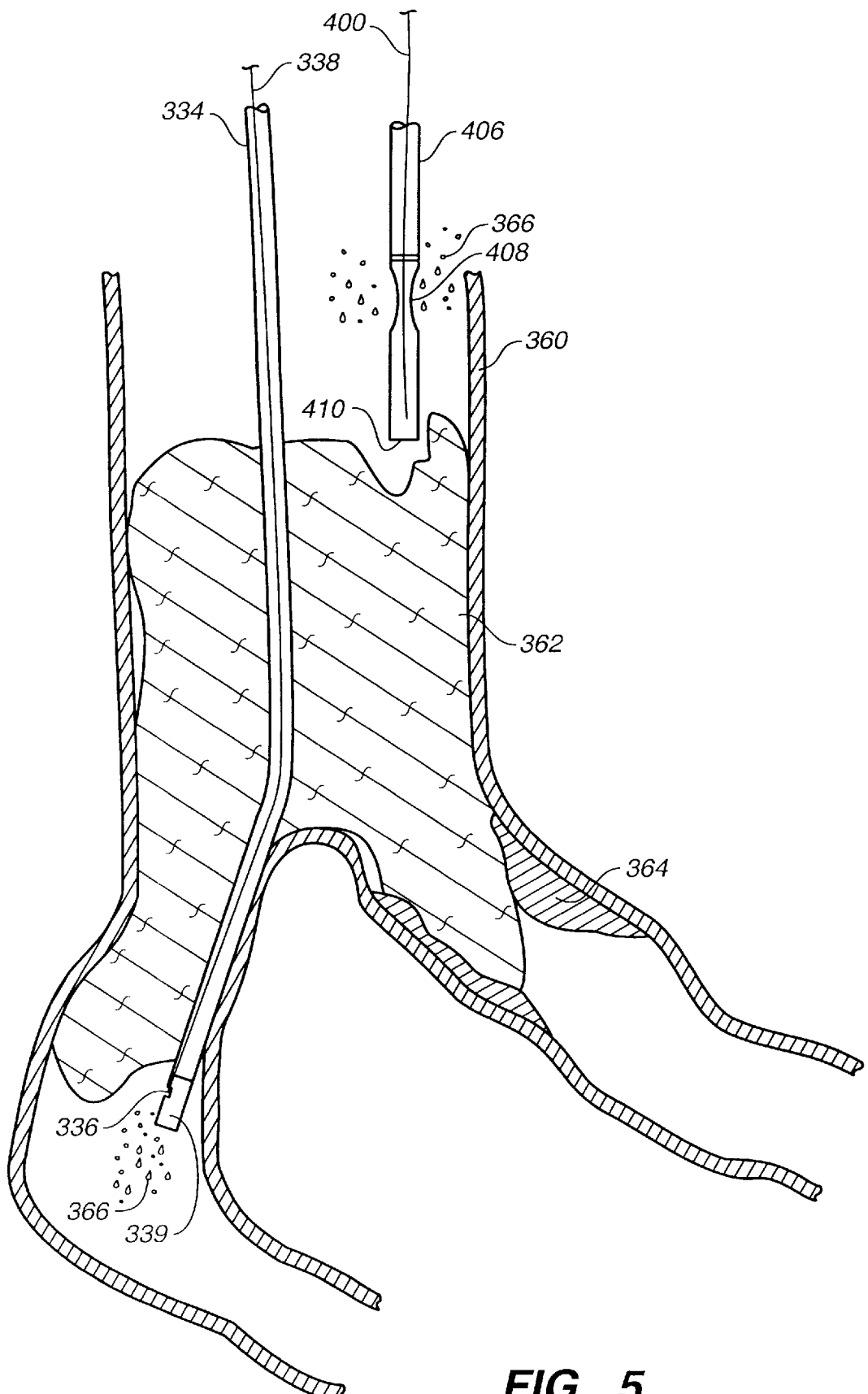
FIG._5

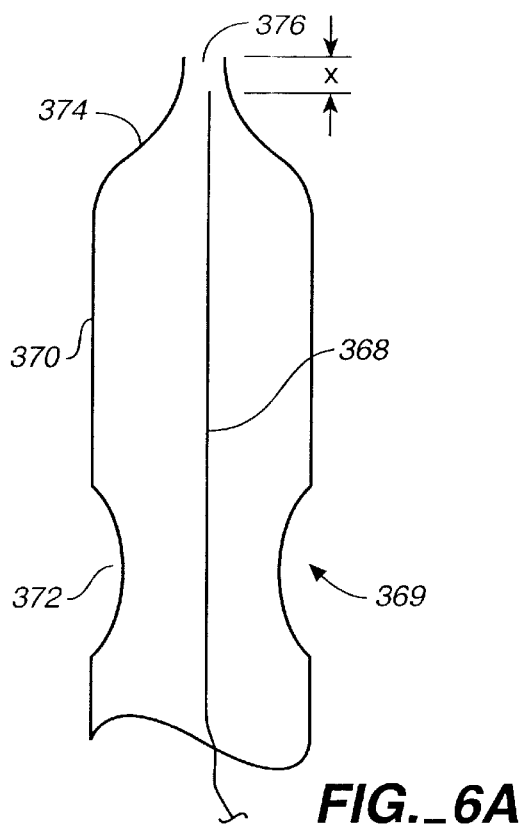
FIG._6A
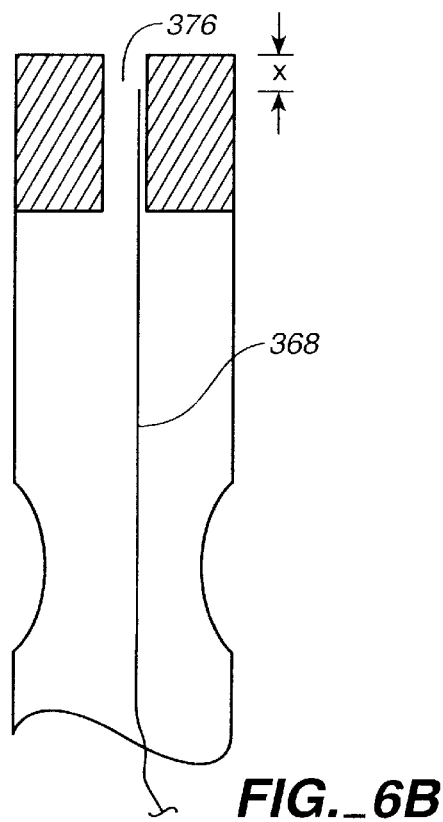
FIG._6B
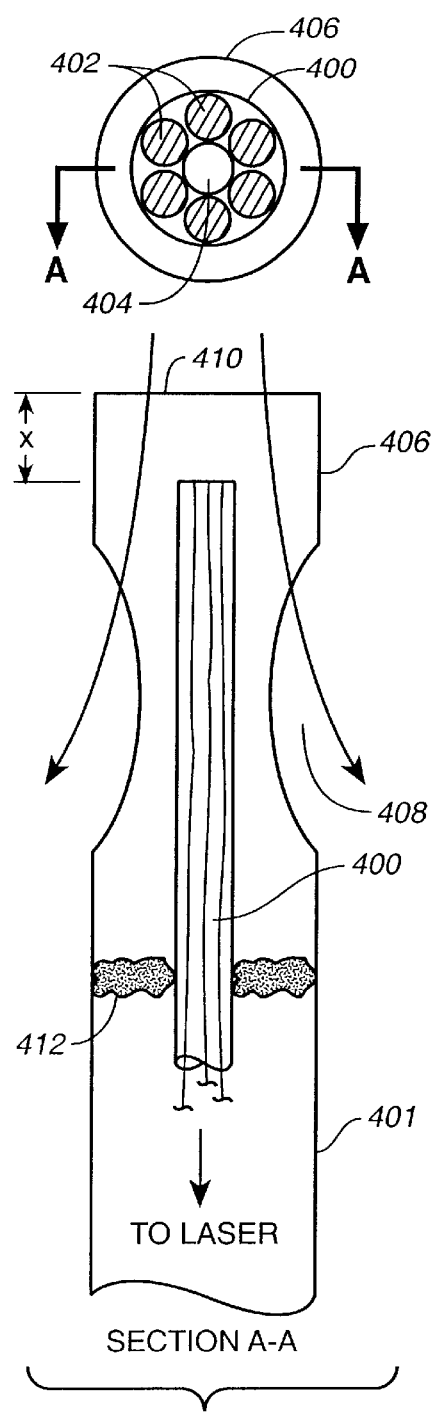
SECTION A-A
FIG._7

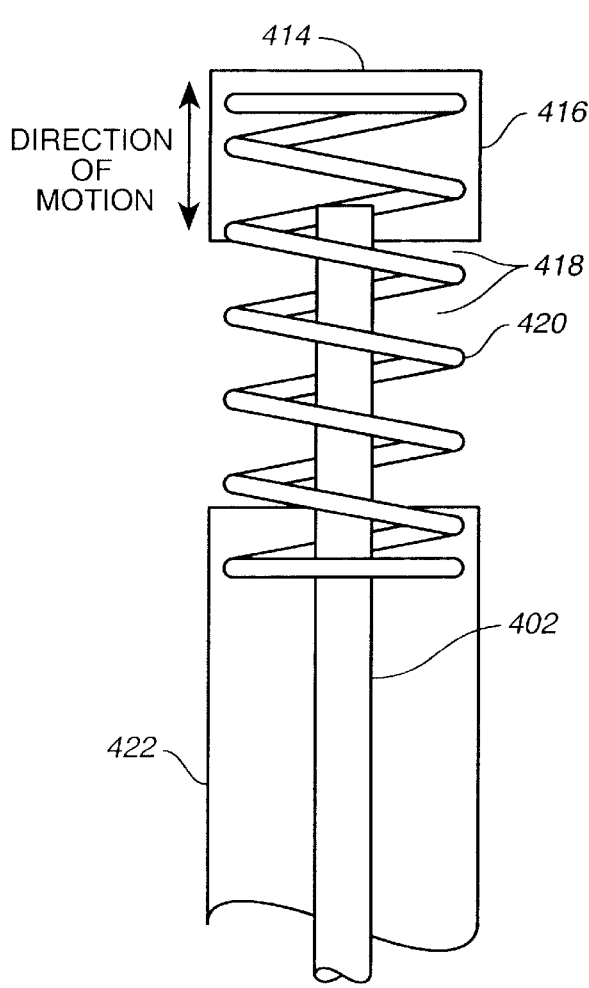
FIG._8
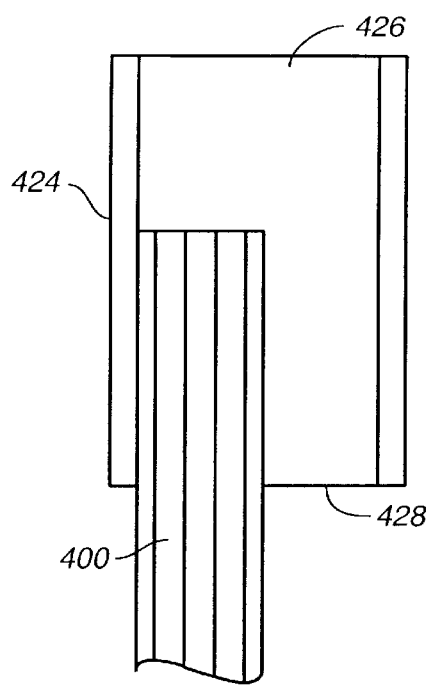
FIG._9
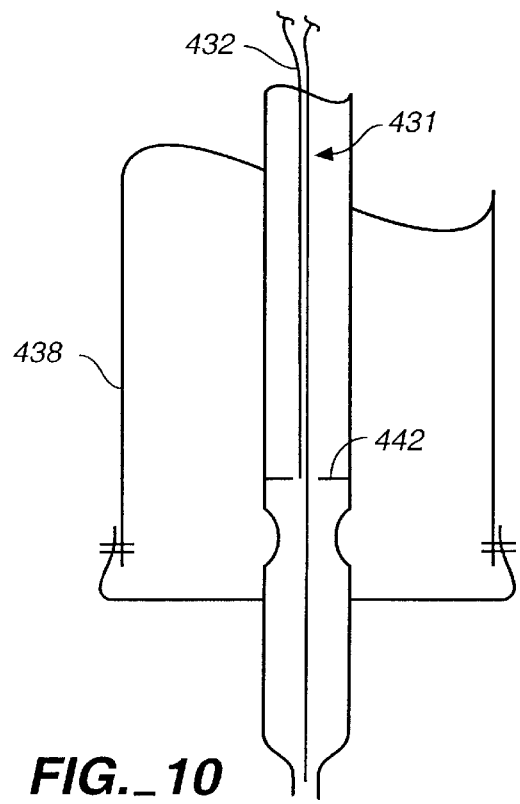
FIG._10

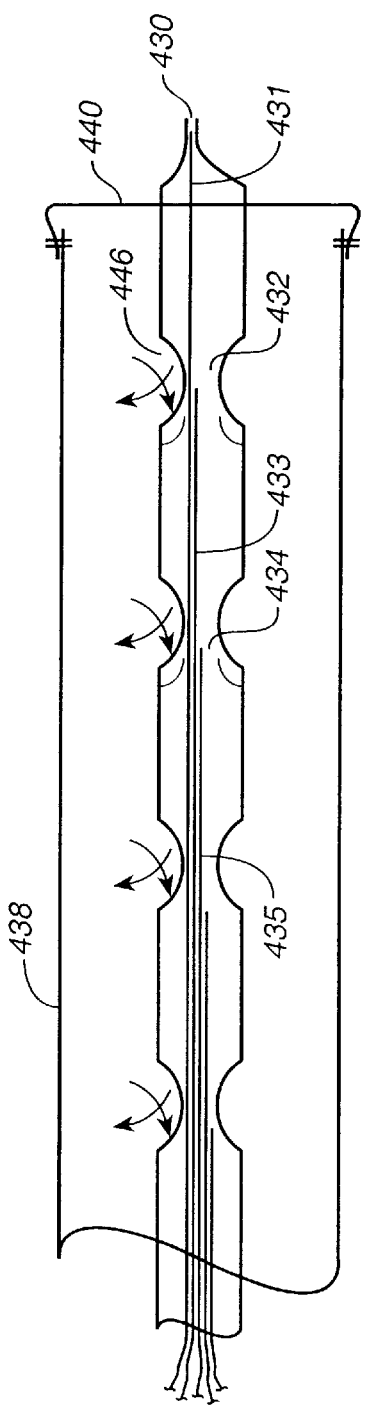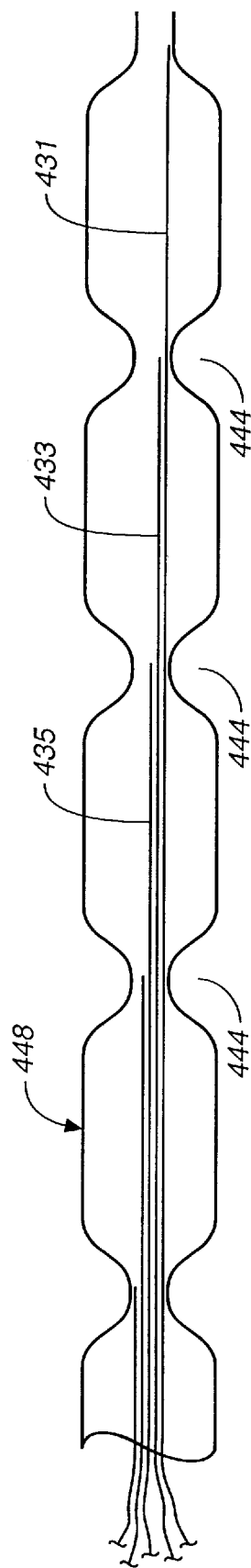

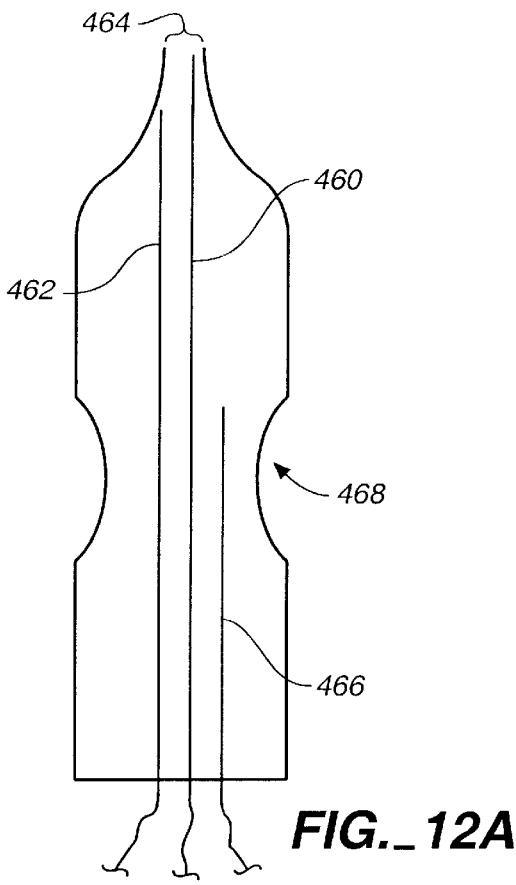
FIG._12A
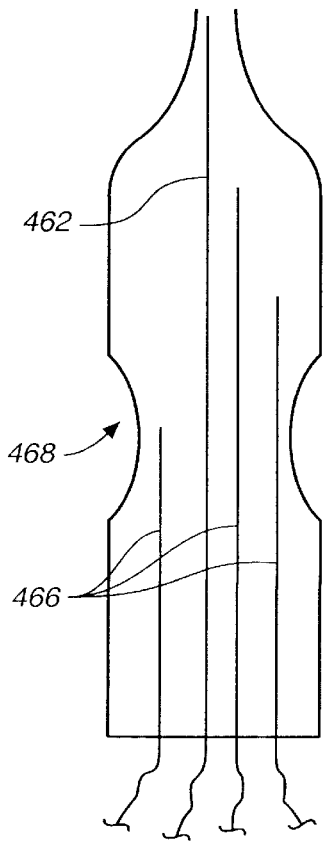
FIG._12B
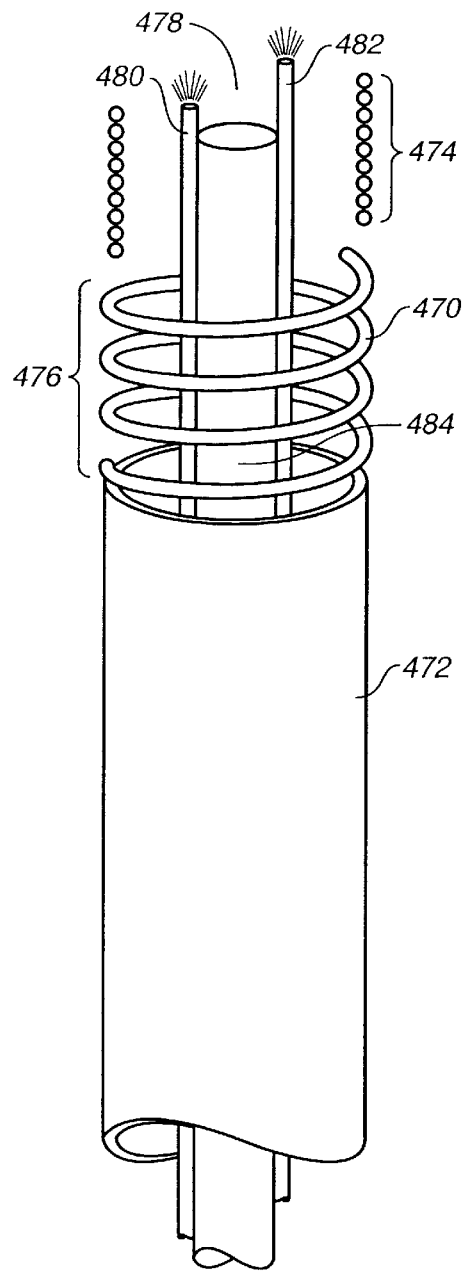
FIG._13

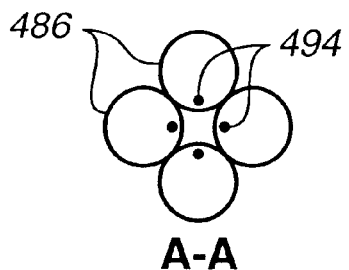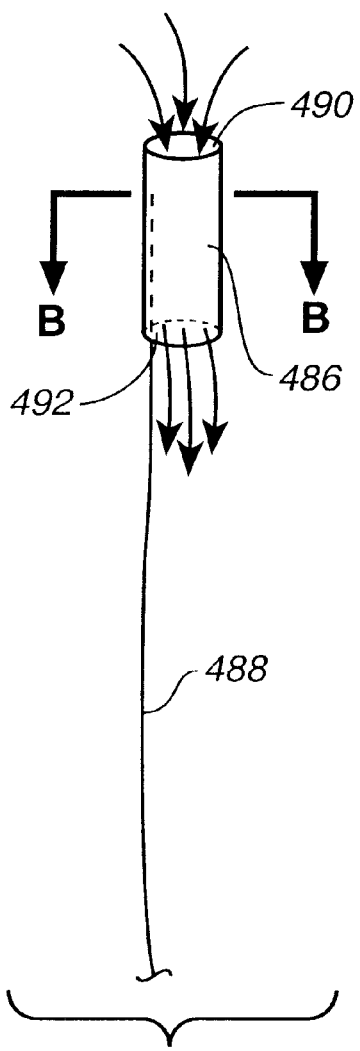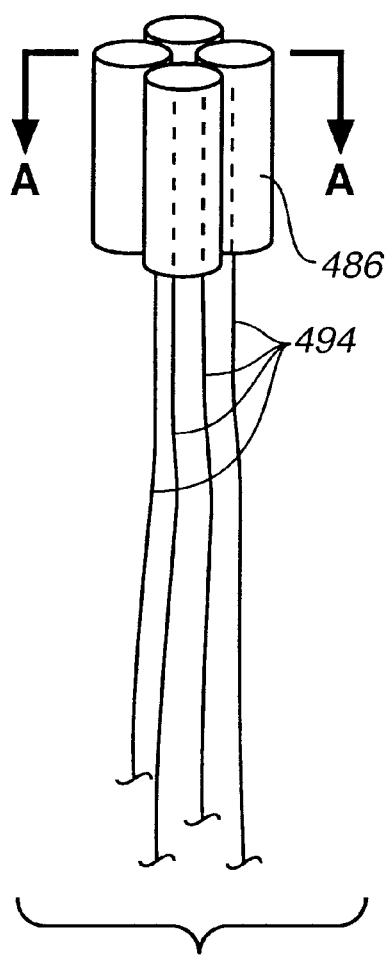
FIG._14A        FIG._14B

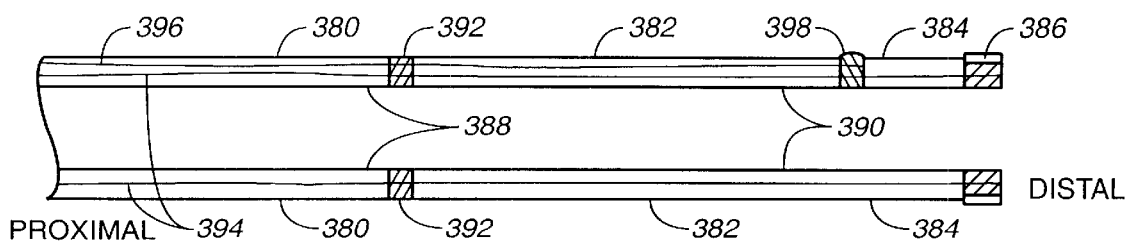
FIG._15A
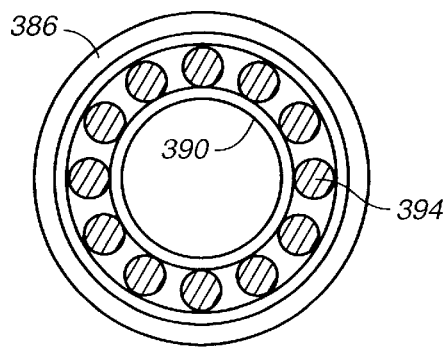
FIG._15B
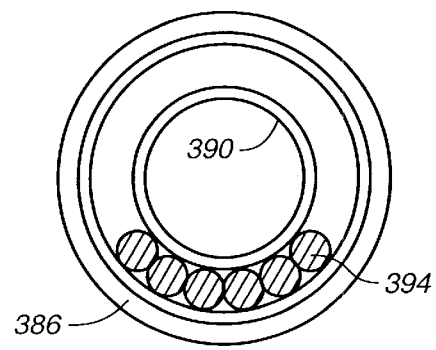
FIG._15C
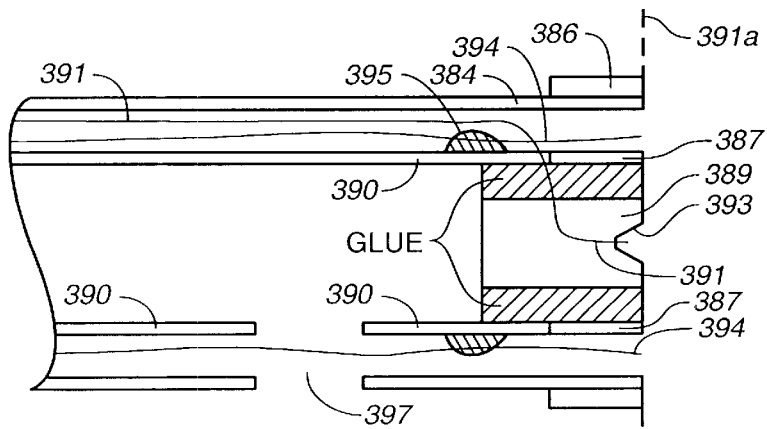
FIG._15D

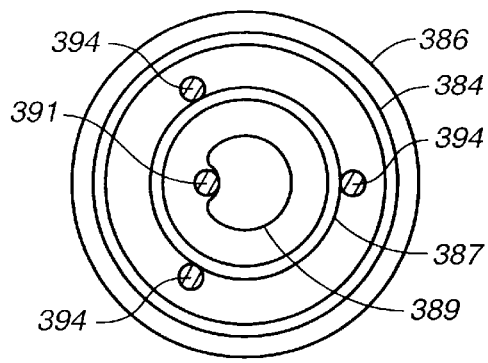
FIG._15E
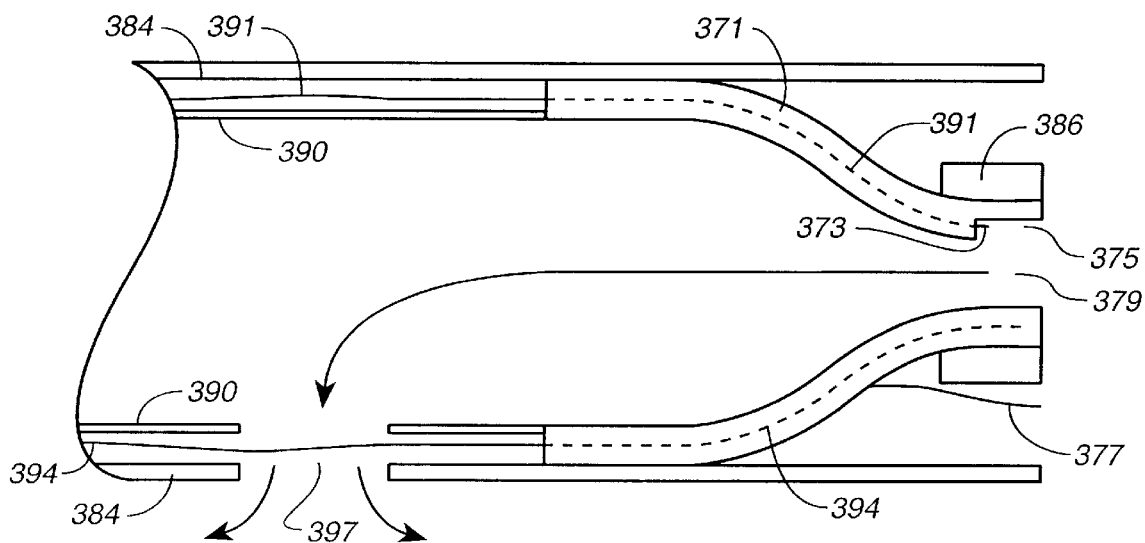
FIG._16A
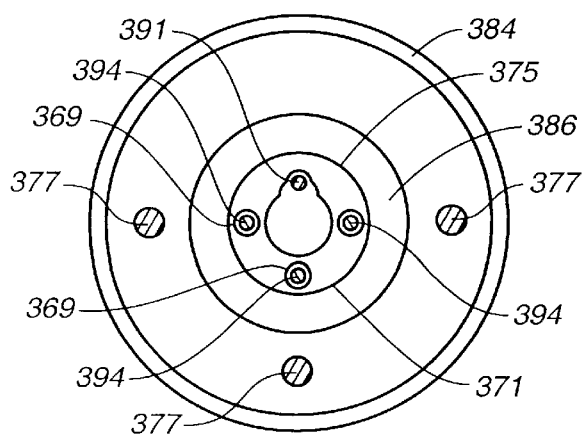
FIG._16B

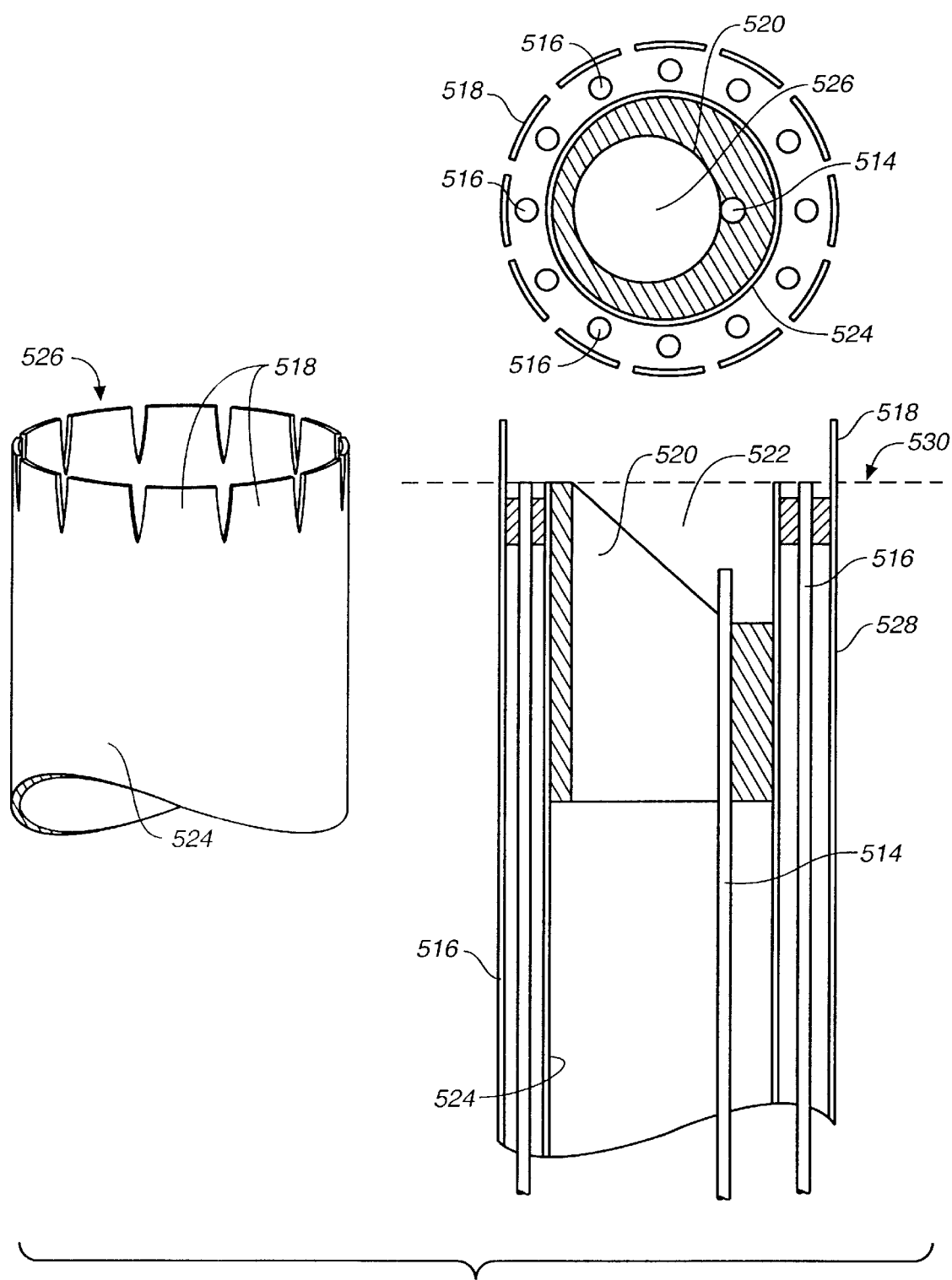
FIG._17

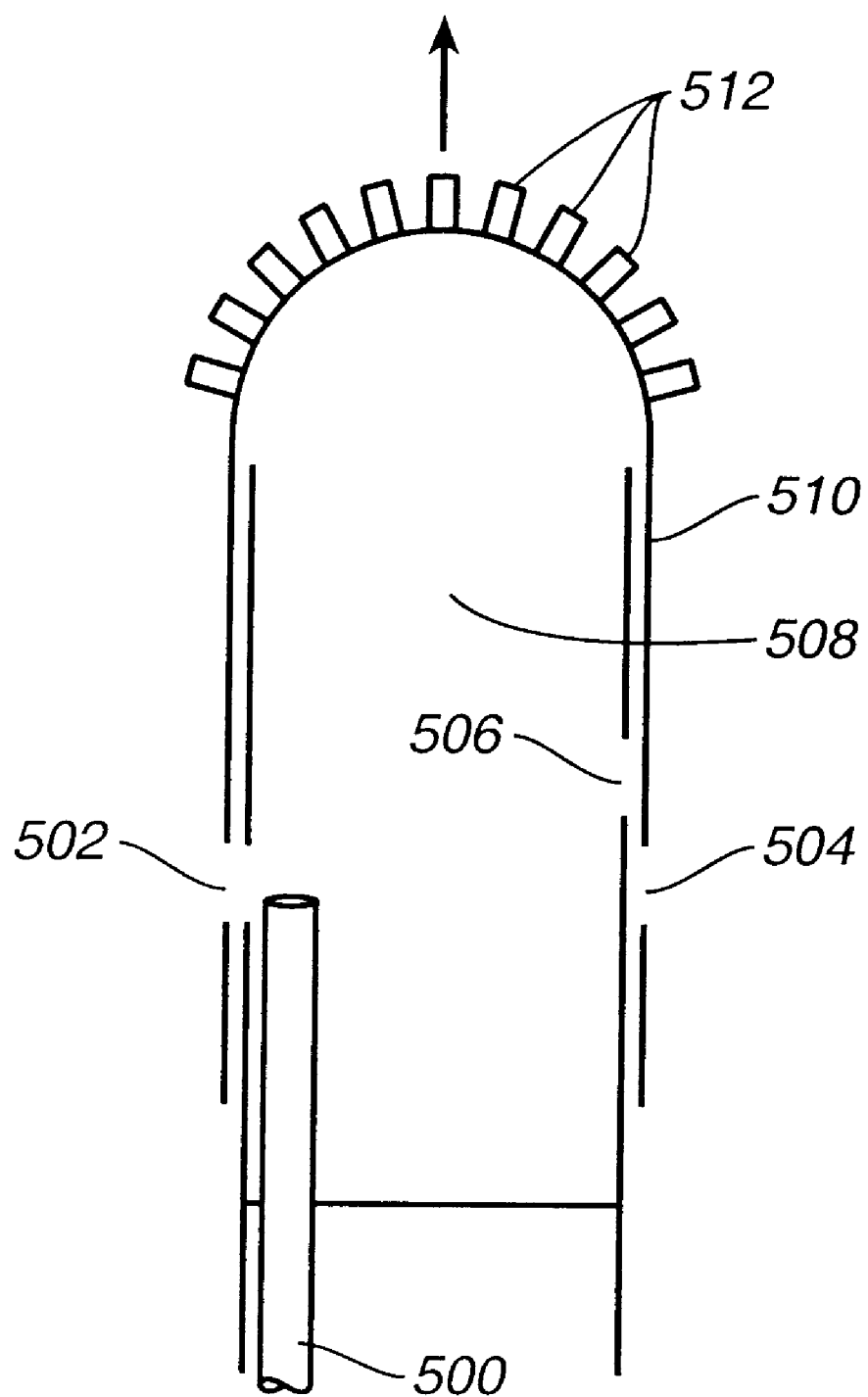
FIG._18

FLOW APPARATUS FOR THE DISRUPTION OF OCCLUSIONS

This is a continuation of application Ser. No. 09/621,247, filed Jul. 21, 2000, now abandoned, which is a division of application Ser. No. 09/120,598, Jul. 22, 1998 now U.S. Pat. No. 6,139,543. This patent application is related to U.S. patent application Ser. No. 08/955,858, now abandoned, entitled "PhotoAcoustic Removal of Occlusions From Blood Vessels," filed on Oct. 21, 1997, and to U.S. patent application Ser. No. 09/113,700, now abandoned, entitled "Apparatus for Delivering Radiation Energy", filed on Jul. 10, 1998, the entireties of both of which are herein incorporated by reference.

BACKGROUND OF THE INVENTION

This invention relates generally to at least partial removal of occlusive material from a body vessel with acoustic phenomena resulting from radiation energy pulses delivered through optical fiber media to the vessel, and, more specifically, to methods and apparatus for generating flow within a body lumen to facilitate disruption of occlusive material and recanalization of the occluded vessel. The term "clot" is used herein to refer to a thrombus, embolus or some other total or partial occlusion of a vessel. The term "emulsify" means to break apart or disrupt by photo-acoustic or mechanical or other phenomena into particle(s) smaller than the original occlusive material.

Various embodiments for delivering radiation energy to body lumens for ablative and photo-acoustic recanalization have been previously disclosed. However, none of these embodiments are capable of generating fluid flow within the vessel that can be used to improve the degree of emulsification of an occlusion.

Therefore, it is an object of the present invention to provide techniques and apparatus that use pulsed radiation energy to generate fluid flow and/or to perform mechanical work within body lumens.

It is another object of the present invention to recanalize body vessels by disrupting total or partial occlusions using the disclosed flow techniques and apparatus.

It is a further object of the present invention to provide improved techniques for removing obstructions from the human body, particularly clots from cerebral blood vessels, without causing collateral damage to the vessel.

It is an object of the present invention to provide a method (and apparatus) for attracting rather than repelling occlusive material to the photoacoustic source of disruption so as to potentially enhance the amount and/or degree of emulsification.

Some or all of these objects are achievable with the various embodiments disclosed herein.

SUMMARY OF THE INVENTION

These and other objects are accomplished by the various aspects of the present invention, wherein, briefly and generally, a device having at least one inlet port, at least one outlet port (which may be distal from or proximal to the external environment), and at least one optical fiber having a distal end positioned relative to the ports such that when pulsed radiation energy is delivered to a body vessel via the optical fiber, fluid is caused to pass through the inlet port and to travel towards the outlet port, preferably past the optical fiber distal end. The repetitive formation and collapse of bubbles in the ambient fluid creates this flow phenomenon, which in turn results from the repetitive absorption of radiation pulses by the fluid. This flow phenomenon can be used to enhance the total or partial mechanical disruption or emulsification of occlusions with photoacoustic phenomena (all of which was previously described in the '858 application) by causing ambient fluid and occlusive material to be drawn towards the recanalization apparatus. The invention can also result in localized emulsification of occlusive material or partial or complete removal of that material from the body. The capability of radiation energy to cause mechanical work to be performed is demonstrated by the present invention.

Multiple fibers can be arranged in such a manner that one or more fibers generate the pumping phenomenon and/or one or more fibers contribute to the clot emulsification by generating the acoustic phenomena described in the previous '858 application, and/or one or more fibers contribute to mechanical disruption of the clot as disclosed herein, for example.

The use of very small diameter optical fibers allows the desired pumping to be achieved and acoustic waves to be generated with a relatively low amount of radiation pulse energy, thereby keeping the amount of heat input to the vessel at a low level. Proper thermal management according to the present invention reduces the likelihood of damaging the walls of the blood vessel adjacent the occlusion, which is especially important for the relatively thin walled vessels of the brain in which the present invention has application. Further, it is desirable that radiation pulses not causing the desired fluid flow or not being efficiently converted into the desired acoustic waves be terminated in order to prevent inputting energy that heats the region without doing useful work, as has been described in both previous applications.

Additional objects, features and advantages of the various aspects of the present invention will be better understood from the following description of its preferred embodiments, which description should be taken in conjunction with the accompanying drawings.

BRIEF DESCRIPTION OF THE DRAWINGS

FIG. 1 is a longitudinal cross-section of a device for demonstrating the capability of the invention to pump fluid.

FIG. 2 includes front and side partial cut-away views of an apparatus for circulating fluid through the distal end of a catheter.

FIG. 3 is a longitudinal cross-sectional view of the apparatus shown in FIG. 2.

FIG. 4 shows end and partial cut-away views of an apparatus for pumping fluid having multiple corresponding side slots and optical fibers.

FIG. 5 shows the devices of FIGS. 2 and 7 disrupting an occlusion blocking a blood vessel, in cross-sectional view.

FIGS. 6A and 6B show simplified cross-sectional depictions of other embodiments for circulating fluid through a catheter tip.

FIG. 7 consists of cross-sectional views of an apparatus for circulating fluid through a catheter tip having a bundle of optical fibers.

FIG. 8 depicts a cross-section of a variable tip catheter for regulating the amount of emulsification of an occlusion, shown in cross-section.

FIG. 9 depicts a cross-section of an embodiment for circulating fluid past a bundle of optical fibers.

FIGS. 10, 11A and 11B are simplified cross-sectional drawings of multiple-stage pumps used to pump fluid from one location to another.

FIGS. 12A and 12B depict simplified embodiments having multiple fibers for performing the pumping and chewing functions of the present invention.

FIG. 13 discloses a partial cut-away of a multiple fiber arrangement with a spring having a variable coil separation forming the distal portion of the catheter.

FIGS. 14A and 14B illustrate side-views of devices that create sufficient jetting/pumping force to pull the fiber along the lumen of a vessel.

FIG. 15A depicts a typical construction, in longitudinal crosssection, for a delivery catheter within the scope of the present invention.

FIG. 15B shows an end-view of a flush fiber arrangement of an embodiment of the invention previously disclosed in the '858 application.

FIG. 15C depicts an end-view of a distal fiber arrangement of the present invention.

FIGS. 15D and 15E detail in longitudinal and radial cross-sections the distal portion of a catheter having a fiber arrangement similar to that shown in FIGS. 12A and 13 within the scope of the present invention.

FIGS. 16A and 16B illustrate in longitudinal and radial cross sections another embodiment of the distal portion of a catheter having a fiber arrangement similar to that shown in FIGS. 15D and 15E.

FIG. 17 depicts a side view and longitudinal and radial cross-sectional views of an embodiment that relies on mechanical action of the distal portions of the catheter to disrupt an occlusion.

FIG. 18 is a simplified depiction of an embodiment that relies on the pumping phenomenon of the present invention to activate a piston-like device that can attack occlusive material.

DESCRIPTION OF THE PREFERRED EMBODIMENTS

The present invention may, in general, be applied to the removal of material forming a partial or total occlusion of any human vessel but is particularly directed to opening a blood vessel that is totally or substantially blocked to the flow of blood. The previously-incorporated patent applications contain adequate descriptions of these general applications of the present invention, as well as the associated preferred configurations and operating parameters of the associated technology, including, for example, the methods and apparatus for delivering radiation energy from the laser to the optical fibers. Those disclosures apply equally to the present invention. However, it should be understood that the present invention is not limited solely to addressing the removal of occlusions from blood vessels but may have much broader applications in which flow is required or desired to be generated, as would be obvious to one of skill in the art upon reading this disclosure.

The present invention encompasses devices, including catheters, having the ability to "chew" through an occlusion by generating flow through an active distal portion to help draw the occlusion towards the optical fibers (and thus towards the source of the acoustic pressure and shock waves and other forces). These catheters promise to be able to create a hole in an occlusion relatively larger than the OD of the catheter or device being used.

Illustrating the types of flow generated by the current invention is the apparatus shown in FIG. 1 comprising an optical fiber positioned inside a capillary tube. Mounting a fiber inside a capillary and firing short duration, low energy, high frequency pulses of absorbable radiation energy creates several useful phenomena. First, generating a series of bubbles 320 inside the sheath portion 322 of the capillary 324 through short-duration, high-frequency, low energy radiation pulses delivered via optical fiber 326 to a fluid medium 328 capable of absorbing said radiation results in a rather violent fluid jetting from the distal end of the capillary in the direction shown by arrows 330. This is believed to result from the expansion of the bubble out of the capillary and into the surrounding media, forcing outwards the slug of fluid that originally occupied the portion of the capillary between the fiber tip and the distal end.

Second, a rather vigorous pumping action was observed during the delivery of pulses of radiation to the fluid, in which fluid shot out of the top of the capillary as indicated by arrows 332. It is believed that this pumping action resulted from the repetitive collapse of bubbles. It is believed that bubble collapse created a zone of low-pressure inside and adjacent to the distal portion of the capillary, which in turn caused surrounding fluid from the vessel to rush back into the capillary to fill the void left by the collapsing bubble. It would appear easier for fluid in the vessel to fill the void rather than fluid already present between the capillary wall and the fiber, because the former would experience less resistance to flow. It is believed that this rapid fluid refilling of the void facilitated the observed flow out of the proximal end of capillary. Capillary action may also have played a role in this first embodiment, although capillary action is not necessary to generate fluid movement, as further explained below.

These pumping/sucking phenomena can be utilized in a variety of apparatus within the scope of the present invention. One such apparatus is shown in FIG. 2. Outer sheath 334 surrounds one or more optical fibers 338 (three are shown for illustration) asymmetrically arranged in the sheath. The distal tips of the fibers 338 are positioned relative to sheath side slot 336 in such a way that fluid present in the vessel is sucked through side slot 336 and forced out the distal end of the sheath 340. The dimensions of the side slot relative to the fiber size and. position are important, since if the fibers are located incorrectly, the pumping/sucking phenomenon is not observed. Satisfactory results are achieved with 12 50/55/65-micron fibers aligned side-by-side, with their distal tips even and extending about ⅓ mm (A) into a ⅔ mm-deep slot (A+B), which was ⅓ mm (C) from the distal tip of the 3French catheter of 0.022 inch inner diameter. The slot was horizontally-sized to match the width of the 12-fiber bundle.

More particularly, 25 ns pulses (separated by about 200 microsecond delays) of 532 nm wavelength radiation (selected for its absorption characteristics in blood) at a frequency of about 1 to 10 kHz (with 5 kHz preferred) were introduced through each of the twelve fibers in bursts of 1–3 pulses per fiber with an energy/pulse of about 100 to 300 microJ and an average power of about 300 milliW. A frequency-doubled Nd:YAG laser was used to produce the desired wavelength light. Clot adjacent slot 336 was sucked into the catheter and emulsified via a combination of shock and acoustic waves and turbulence caused by the expansion and collapse of bubbles in the fluid. The emulsified material was then directed out of distal tip 340 and back into the fluid. It is believed that the edge of slot 336 also contributed to the emulsification by tearing the clot as it entered the turbulent region adjacent the optical fiber tips. This mechanical disruption by the edge also resulted from the bubbles hammering the clot against the edge during emulsification. As with all embodiments of the invention, however, the laser parameters, such as for example the pulse duration (for example between 5 and 30 ns), the wavelength, and the pulse energy, may be varied while still producing the desired phenomena.

The sucking motion at slot 336 creates a small vortex which circulates the emulsified material exiting end 340 back towards slot 336 as distance C approaches less than 0.25 mm. This vortex action appears to help keep the clot in contact with the slot once the clot is first sucked in, and thus aids further emulsification.

FIG. 3 is a sectional view of a side-sucking apparatus similar to that shown in FIG. 2. Distal tip 339 containing slot 336 is shown attached to outer catheter wall 334, typically with glue such as cyanoacrylate. The distal end of optional inner lumen walls 354 can terminate evenly with the tip of optical fiber(s) 338, which makes polishing of the fiber and catheter tips during catheter construction easier. As shown in FIG. 3, the volume of the outlet port 340 can be decreased to form annular space 356 by inserting mandrel 350 through inner lumen 352 formed by inner lumen walls 354. Decreasing this volume increases the velocity with which the emulsified clot is expelled from the outlet port 340. Typical materials of construction for the distal tip 339 include HDPE, LDPE, PET, polyimide, or even a metal. Typical distal dimensions are those of a 3French catheter, although proportionately larger or smaller devices may be constructed depending upon the size of the vessel to be accessed.

An example of a catheter that may be used to deliver the embodiment shown in FIG. 3 as well as other embodiments of the invention to the occlusion site is shown in FIG. 15A. The delivery catheter may comprise two concentric tubes. The outer and inner tubes may comprise multiple sections of decreasing flexibility. As an illustration, FIG. 15A shows three outer sections and two inner, although other combinations may be used. In a 150 cm catheter, for example, outer sections 380, 382, and 384 may be anywhere from about 50–120 cm, about 25–95 cm, and about 3–20 cm, respectively. Sections measuring 100 cm, 45 cm, and 5 cm, for example, produce satisfactory results. A satisfactory proximal outer section 380 comprises a composite of polyimide/spiral stainless steel tubing, with an inner diameter, for example, of 0.030 to 0.040 inches, such as that made by Phelps-Dodge High-Performance Conductor. Section 380 is glued with, for example, cyanoacrylate glue 392, to mid outer section 382 comprising high-density polyethylene (HDPE). The HDPE facilitates joining the more rigid composite proximal outer sheath to the soft distal outer section 384, to which section 382 is heat-fused. Section 384 comprises plasticized polyvinylchloride (PVC) of 60–65 shore A hardness. The inner tube comprises heat-sealed sections 388 and 390 having lengths of anywhere from about 120–140 cm and about 10–30 cm, respectively. Proximal inner section 388 has a material selected to provide the desired rigidity and high burst pressure, such as polypropylene tubing with flexual modulus (psi) of between about 200,000 and about 250,000, with about 220,000 being typical. Distal inner section 390 may comprise a LD polyethylene/EVA blend. A 9% EVA/LD polyethylene blend is satisfactory. To facilitate fluoroscopy, a radioopaque band marker 386, of gold or platinum, may be added to the distal tip of the catheter. The marker band is glued to the distal outer tubing, either outside of the distal outer portion or abutted against the distal edge to be flush with the outer wall. In general, the inner tube materials are chosen for their burst properties, lubricious characteristics and the outer for their rigidity or softness. Similar materials having similar relative flexibilities, softness, and lubricious properties may be substituted for those disclosed for the inner and outer tubes, as one of ordinary skill in the art would recognize. Fibers 394 lie freely between the inner and outer concentric tubes, anchored in place only by the various glue points shown to facilitate increased flexibility. A more rigid catheter may be achieved by injecting more glue at various points between the two tubes of the constructed apparatus. One or more stainless steel or nitinol mandrel 396 may also be inserted between the inner and outer tubes to create more rigidity. The mandrel may be anchored in place by glue points 392 and 398. A mandrel of 0.004 inches diameter may be used, although other diameters or a tapered mandrel would be acceptable, depending on the desired degree of rigidity/flexibility of the construction.

A lubricious polymer coating, such as a hydrophilic coating or silicone may be used to increase the ease of navigating the catheter through the guiding catheter and desired body lumens, and if introduced on the interior catheter walls, may enhance the trackability over an associated guidewire.

In general, catheter construction is well-known to those of skill in the art and thus will not be described in great detail. In brief, after inserting the desired number of optical fibers and the inner tubular member into the outer tubular member, the distal location of each fiber is adjusted so that the fiber distal ends occupy the desired distal geometry. For example, the fibers can be sequentially arranged in the same order as in the planar array of connector 310, so that they occupy the geometry shown in FIG. 15B (as an example of a configuration that could be used for the embodiments disclosed in the previous '858 patent application) or in FIG. 15C (that would correspond to the embodiment shown in FIGS. 2 and 3). To accomplish this, a light source, such as a marker laser, is used to identify which fiber distal end corresponds to which fiber end positioned in the connector. As each fiber is sequentially identified, its distal end is temporarily held in position until all fibers have been identified and located. The fibers are then glued into position. Fibers can be held temporarily in position by inserting each distal end into an alignment block having a series of holes, each hole corresponding to a particular fiber. The block holds the fibers in position until they are glued.

Fluid such as biocompatible coolant (e.g., saline), radiographic agent or thrombolytic agent may be introduced through inner lumen 352 during emulsification. Or, alternatively, fluid may be aspirated through the lumen to remove emulsified material from the body.

FIG. 4 depicts a catheter in which multiple fibers are mounted approximately equidistant around the circumference of the catheter, each fiber having its own inlet port in the side of the catheter tip. When the fibers are fired individually with pulsed radiation, as described herein, each fiber creates its own pumping action through its corresponding side hole 358. As the position of the distal tip of an optical fiber moves up its side hole towards the catheter's distal tip, the pumping phenomenon tends to change from sucking through the side hole to blowing out of the side hole. When the tip of the catheter is located in fluid adjacent the occlusion, such an arrangement of fibers can cause the end of the catheter to gyrate around the clot, thereby increasing the degree of emulsification of the clot relative to a catheter that remains relatively stationary. Gyration can be improved by decreasing the number of fiber-and-slot combinations and increasing the number of consecutive pulses to each fiber, to permit the catheter tip to overcome inertia and to move through the fluid across the face of the clot. Gyration, however, is minimized if the catheter tip is located within an occlusion, due to high damping forces.

FIG. 5 shows how the device depicted in FIGS. 2 and 3 may be used in a blood vessel 360 having a thrombus 362 and stenotic plaque 364. For the device shown in FIG. 2, the catheter can be punched through the thrombus while the optical fibers are dormant until the catheter reaches the distal position shown. Pulsed radiation is then delivered down one or more optical fibers 338, causing the thrombus to be sucked into slot 336, emulsified, and then ejected 366 through the catheter distal tip. During the procedure, the catheter tip is slowly withdrawn through thrombus 362, thereby revealing new thrombus to the catheter tip for emulsification. The speed of withdrawal is dependent upon the character of the thrombus being emulsified and the geometry of the fibers and slot. The catheter should not be withdrawn so fast that the catheter's ability to chew through the thrombus is overwhelmed and the catheter tip becomes clogged, thereby adversely affecting the degree of emulsification. While FIG. 5 depicts thrusting the catheter tip of FIG. 2 entirely through the thrombus before emulsification begins, it may also be used to emulsify thrombus by simply causing the catheter tip to approach the proximal portion of the thrombus with the optical fibers already firing into the ambient fluid so as to create the desired acoustic phenomena and avoid direct ablation.

Another apparatus that exhibits the pumping/sucking phenomena is shown in FIG. 6A. Instead of a side-sucking apparatus, however, examples of which are shown in FIGS. 2 and 3, FIG. 6A depicts an apparatus that sucks through distal port 376 and discharges through rear ports 372. Optical fiber 368 is positioned within lumen 370 such that the distal tip of fiber 368 is located between distal opening 376 and rear openings 372, and within sufficient distance of distal opening 376 such that pulses of radiation delivered through optical fiber 368 cause fluid adjacent the distal port 376 to flow into the catheter and out of the exit ports 372.

The tapered portion of FIG. 6A has the advantages over a wider intake port, for example, up to about 400 microns and shown, for example, in FIG. 7, of increasing the ultimate velocity of fluid-intake through the distal opening 376 and of minimizing the possibility of permitting clot to by-pass the emulsification zone at the optical fiber tip(s). A typical necked portion of tubular member 370 can be formed, for example, by gently pulling heated PET tubing until it elongates and creates a portion of narrower diameter, and then cutting the narrower portion to form the distal opening 376. Distal openings of from about 0.008 to 0.012 inches or larger can be made from 0.029 inch ID PET tubing. The necked portion typically extends over about 1 mm.

FIG. 6B depicts an alternative method of narrowing the distal inlet portion of a tubular member. Instead of necking the member, a simple doughnut-shaped object with desired inner diameter is glued to the distal end of the member. Such object may be of any suitable material, such as polyimide or polyethylene tubing or some other polymeric material.

For front-sucking devices such as shown in FIGS. 6A and 6B, the positioning of the distal tip of the optical fiber relative to the distal opening become more sensitive as the distal opening diameter increases. That is, the wider the opening, the smaller must be x. A typical dimension between the fiber tip and the plane of the distal port 376 (x) for a 0.008-inch wide distal port and a 50-micron in diameter optical fiber and the operating parameters disclosed herein, including energy per pulse of about 200 microJ, is between about 100 and 350 microns. However, as the distal port diameter increases to about 0.015 inches in diameter, the tolerance range decreases to between about 100 to 150 microns, or 0.004 to 0.006 inches.

It is believed that this increase in positioning sensitivity for wider distal ports is related to the ability of a generated bubble to fill the space between the walls of the distal opening and thus to generate the pumping force. That is, for the same operating conditions and bubble volume, a bubble spanning the distal port would have a smaller depth (and thus a smaller range of x) for a larger crosssectional area tube than a bubble filling a smaller cross-sectional area tube. Since the size of a bubble also depends upon the amount of energy delivered to the absorbing fluid, however, the sensitivity in relative positioning between the fiber tip and the distal port can be decreased by increasing the energy per pulse, and thus the size of the bubble generated per pulse.

FIG. 7 depicts another embodiment of the invention, in which a bundle of multiple fibers 400 (with six optical fibers 402, for example, together with a central lumen for delivering fluid (for example, coolant) to, or aspirating fluid from, a blood vessel) is shown positioned within an outer sheath 406 between the one or more side slots 408 and the distal opening 410. If the fiber bundle 400 is positioned centrally within sheath 406, as shown, it may be secured in place with a glue plug 412. When pulses of radiation are delivered through the optical fibers in sequence to a fluid capable of absorbing the radiation, such that a series of transitory bubbles are first generated and then collapse, flow is created from the distal opening 410 past the distal end of the fiber bundle 400 and out of the oval side slots 408, as shown by the arrows in FIG. 7. Typical dimensions for this construction include 5 mm for the portion of the catheter between the distal opening 410 and the distal edge of the side slot 408; typical side slots 408 can be between 5 mm and 10 mm; for a fiber bundle of outside diameter of between 0.01 and 0.02 inches, a catheter tip diameter of about 1 mm (or 0.04 inches) was used. For the construction described herein to generate flow as described, the dimension labeled x between the distal tip and the tip of the optical fibers was between about 0.004 and 0.006 inches. Typical materials of construction for the sheath are HDPE or PET or polyimide. As shown, sheath 406 optionally may comprise part of catheter 401, which serves as the delivery vehicle for positioning the apparatus adjacent an occlusion. However, catheter 401 is not necessarily required, as long as some other sufficiently rigid and sufficiently flexible delivery means, such as the fiber bundle 400 itself, is available.

A typical construction for the fiber bundle comprises a proximal portion having a spiral-wrap stainless steel coil sandwiched between polyimide tubings, together with an outer layer of shrink-wrapped PET as desired, and mid and distal portions having successively fewer layers of polyimide. The desired distal portion of acceptable outside diameter of between 0.01 and 0.02 inches (0.018 inch being preferred) comprises optical fibers positioned with cyanoacrylate glue between either two concentric polyimide tubes or one inner polyimide tube and an outer platinum coil. Coolant or other fluid may be introduced through the inner polyimide tubing as desired or emulsified material can be aspirated.

The apparatus shown in FIGS. 6 and 7 may be used to emulsify an occlusion, by drawing the occlusion through the distal opening towards the optical fibers and emulsifying it in the manner described herein and as shown in FIG. 5. More specifically, the apparatus depicted in FIG. 7 is shown in FIG. 5 attacking the proximal surface of occlusion 362. Emulsified clot 366 is shown ejected from side slots 408 after being emulsified through a combination of shock wave and forces generated by the expansion and collapse of transitory bubbles, all as described in the earlier applications. Again, the user should take care not to push the apparatus of FIGS. 6 and 7 too quickly through the occlusion during emulsification, so as to avoid overwhelming the apparatus.

The apparatus depicted in FIG. 8 addresses this potential issue by regulating the amount of clot being emulsified in the apparatus and thus helping to prevent the optical fibers from being overwhelmed and the device from plugging. It comprises a variable size exit port (created by a loosely-coiled spring) that permits the apparatus either to suck or repel the clot surface. A stainless steel spring 420 is glued to the distal end of the main catheter body 422. To the distal end of spring 420 is glued a sheath 416 of polyimide or HDPE. Single optical fiber 402 is positioned as shown such that the sheath 416 covers its tip. The tip of the optical fiber is positioned relative to the distal end of the sheath tip such that flow is generated through distal opening 414 when radiation pulses are delivered through the optical fiber 402 to the site of the occlusion. Lumen fluid and gelatinous clot are sucked through frontal inlet portion 414 of the distal catheter tip 416 toward the optical fibers and emulsified as described herein, and then are ejected through the open portion 418 of the spring 420. As the clot is pulled into the front portal 414, however, the clot presses against the outer surface of the distal sheath 416 of the apparatus, slightly compressing the spring 420. The resiliency of the spring then biases the distal sheath 414 away from the clot, thereby decreasing the amount of clot being pulled into the device to be emulsified. As the device is moved away from the clot, the suction caused by the absorption of radiation energy into the lumen fluid again draws the clot towards the device and so continues the emulsification. In this manner, the user is aided in controlling the rate of emulsification through the apparatus' constant minor adjustments. Although only a single fiber is illustrated in FIG. 8, multiple fibers or a fiber bundle would also work for this embodiment. Again, although this embodiment is shown mounted on a catheter 422, if no fluid needs to be delivered through a central lumen to the activity site, as in most of these embodiments, then a catheter is not required to deliver the apparatus to the occlusion. Instead, any appropriate, sufficiently-flexible means such as a simple wire, may be used to deliver the active portion of the apparatus to the occlusion. A typical outer diameter of this apparatus would be between about 0.010 and 0.020 inches, with a preferred outer diameter of about 0.018 inches. Portion 416 can be constructed out of any appropriate material such as polyimide.

Spring 420 should have a spring constant k sufficient to prevent the fiber tip from directly contacting the clot as the clot gently presses against the outer surface of the distal sheath 416, so that a distance is ideally maintained between the tip of the fiber bundle 400 and the outer edge of distal sheath. This distance may approximate 0.004–0.006 inches for a 1-mm diameter sheath and optical fiber bundle of between 0.01 and 0.02 inches outside diameter. If the spring is so weak that the spring permits the optical fiber tips to travel beyond the spring/distal sheath arrangement, then this variable tip, spring-loaded apparatus can lose its advantage of controlling the rate of emulsification and its ability to pump. A satisfactory spring for this purpose may be made by winding about 140 kpsi Ultimate Tensile Strength stainless steel or platinum wire of about 0.002 to 0.003 inches diameter around a mandrel, and then stretching a section so that between about 5–10 windings occupied about a 5 mm length. Obviously, other materials and dimensions would produce other satisfactory springs to serve the purposes described.

The apparatus shown in FIG. 9 can establish either forward or reverse flow depending on the position of the tip of the fiber optic bundle 400 relative to the distal opening 426. When the fiber optic bundle 400 is positioned within about 0.004 to 0.006 inches from the distal opening 426 of the HDPE 1-mm diameter sheath 424, suction is developed through opening 426 and fluid is expelled through rear opening 428. Alternatively, if the distance between the distal tip of the fiber optic apparatus is either increased or decreased outside of the 0.004 to 0.006 inch range, the flow mechanism reverses, and the device develops suction through opening 428 and expels fluid through distal opening 426. The same would be true for differently sized devices, as long as the bubble size produced by the fiber/energy/ operating conditions combination were sufficiently large. Preferred constructions of catheter tips for preferred single-stage pumping/sucking/emulsifying embodiments of the present invention have been described. FIGS. 10, 11A and 11B depict multistage embodiments within the scope of the present invention. Multiple single stages 369 of the type depicted in FIG. 6 are connected end-to-end to create a multiple-stage fluid pump of FIG. 11A. Fluid sucked through distal end 430 and into the first unit as a result of radiation delivered to optical fiber 431 is then sucked from the first unit through opening 432 and into the second unit by the action of optical fiber 433. Fluid in the second unit is then sucked through opening 434 and into the third unit by the action of optical fiber 435, and so on. In this way, fluid passes from distal opening 430 down the length of the multistage pump. FIG. 10 depicts each stage separated with a simple doughnut-shaped plate 442 rather than a nozzle 374. Firing of the various fibers should be controlled so that radiation is delivered to each fiber tip only when the tip is immersed in fluid. This can be assured by priming the apparatus before use with fluid similar to the fluid in which the distal port is immersed, or firing the fibers only when the fluid pumped from the vessel reaches each fiber. FIG. 11A depicts the multistage pump with each stage having exit slots 446. FIG. 11B is depicted with no exit slots. Instead, elements 444 are necked portions of the outer tubing in which the fiber tips are positioned to generate the sucking/ pumping force. Such necked portions can be formed by heating and collapsing the polymeric tube 448 around a central mandrel, and then, after cooling, removing the mandrel to leave the tube with multiple collapsed portions. The fibers are then positioned and secured inside each necked portion to form the multistage apparatus.

The apparatus of FIGS. 10 and 11A are depicted housed inside optional tubular vessel 438 sealed on its distal end with impervious webbing 440. Tube 438 would contain any fluid pumped from the vessel in which the apparatus is positioned and prevents the pumped fluid, including any emulsified clot, from passing back into the vessel. Further, while each stage depicted has side slot in fluid communication with tube 438, such slots are not required.

Optionally, each stage could be separated by a valve— e.g., a leaf valve or a ball valve (not shown)—to prevent backflow from stage to stage or to direct or rectify fluid flow in a particular path. Such valves could also be used on the single stage versions, for example to seal off the exit port as the fiber was firing to ensure that fluid was pumped into the device only through the inlet port.

The pump head developed by a device such as that shown in FIG. 6A can be determined by positioning that apparatus with its exit ports 372 inside the tube-and-webbing arrangement shown in FIG. 11A. Fluid pumped from a source will slowly fill the tube until the height of the fluid equals the pressure developed by the pumping mechanism. A single optical fiber has generated heights of water equivalent to between 0.25 to 0.5 psig. In addition, even for a nonoptimized set-up, pumping rates in the order of about 0.2 cc/second were observed for an average power of about 300 milliW.

Traditionally, pumping or suction of fluid within the body has been achieved by having an external source of suction or pressure generate a corresponding negative or positive pressure inside the body cavity. The fluid jetting/suction phenomenon of the present invention, however, illustrates how fluid can be pumped inside the body cavity (or in any other remote source of fluid) using radiation energy from a radiation source remote from the point of fluid flow. Pumping fluid using the methods described is believed to result in relatively high, albeit fleeting, pumping pressures of perhaps several hundreds of psig. Such pressures were previously unattainable in the body without risk of injury.

FIGS. 12A and 12B show various fiber arrangements for minimizing the ability of non-emulsified clot sucked into the apparatus through the distal opening from escaping emulsification before being ejected through the side slots. Multiple fiber arrangements have the advantage of permitting the various functions of sucking and chewing/emulsifying to be performed by different fibers. For example, in FIG. 12A, fiber 462, positioned relative to the distal opening 464 as described above for FIG. 6A, creates the pumping/sucking force drawing fluid and clot towards the distal opening 464. Fiber 460, positioned flush with, or slightly past distal opening 464, performs the function of emulsifying the clot but is incapable of contributing to the pumping phenomenon because of its location. This initial emulsification at the distal opening by fiber 460 helps to increase fluid flow through the opening, which in turn helps to cool the distal end of the apparatus. Of course, fiber 462 may also contribute to the actual emulsification in addition to creating the fluid flow, because of the accounting phenomenon being generated by the repetitive pulses of radiation energy.

Fibers 466 perform further emulsification of clot particles as they travel through the apparatus towards the side slots 468. However, if the fiber tips are longitudinally spaced too closely together, then it may be possible that during the inactive period between pulses of treatment laser radiation, clot particles that could benefit from further emulsification might actually avoid further emulsification because of the fluid velocity created by the apparatus' geometry and operating conditions. Thus, fiber tips ideally are positioned longitudinally relative to one another such that clot particles are incapable of bypassing all emulsification zones between consecutive pulses of radiation. For a construction of the type shown in FIGS. 6 and 12 having a 0.012 inch diameter distal opening and a nominal 0.022 inch inner tube diameter and a typical energy level as described herein, fluid velocities in the order of 200 cm/sec have been observed. For a period between pulses of, for example, 200 microseconds, typical fiber tip spacings are about 100–500 microns, depending on the duty cycle. That is, the longer between consecutive pulses, the farther apart the fiber distal tips need to be to minimize the chance of a particle avoiding all emulsification zones.

FIG. 13 discloses a variation of the embodiment shown in FIGS. 8 and 12A. Spring 470, shown in partial cutaway to reveal the distal portion of the apparatus, is attached to the distal end of a suitable catheter 472. The distal portion of spring 474 is tightly wound, and serves as a flexible tip to permit the device to navigate the tortuous path of small diameter vessels in order to approach an occlusion. The proximal portion of spring 476 has a larger coil separation than the distal portion 474, and thus provides exit ports between adjacent coils, through which fluid and particles that are sucked in through distal opening 478 and emulsified can be ejected.

Fiber 480 is positioned inside the tightly-wound distal portion 474 of the spring such that pulsed radiation delivered through fiber 480 into the ambient fluid causes the fluid to be pumped through the distal opening 478 and out of the wider spring windings in spring portion 476. Fiber 482 is positioned substantially flush with the distal opening 478 of the spring 470, and thus does not contribute to the pumping action. However, as fluid and occlusive material approach the device due to the sucking/pumping action caused by fiber 480, both fibers help to emulsify portions of the occlusion. Furthermore, consistent with the discussion of FIGS. 12A and 12B, other longitudinally-offset fibers can be positioned inside spring 470 to ensure complete emulsification. The spring described in connection with FIG. 8 would also be satisfactory here. The desired coil separation could be achieved by inserting two razor blades into the spring between coils a certain desired distance apart, and stretching that portion of the spring until the desired linear coil density is reached.

Central lumen 484 is optional, and can be used to deliver fluids such as radiographic contrast agent or coolant to the site of the occlusion. Since all embodiments of the invention rely on the absorption of select wavelength radiation energy into colored fluid such as blood, however, delivering fluid to the area of emulsification that alters the color of the vessel fluid through dilution or dissipation, may interfere with the absorption characteristics of the environment of the occlusion. Small delays in the emulsification process thus may be necessary to permit the area surrounding the environment to reperfuse with fluid, such as blood, that is capable of absorbing the wavelength light being used, if fluid is introduced to the site of the occlusion through the central lumen. Alternatively, a tinted fluid compatible with the ambient conditions of the occlusion, may be introduced, so that absorption of the radiation energy will be minimally affected by the introduction of other fluid.

FIGS. 14A and 14B disclose another embodiment of the invention. As shown in FIG. 14A, cylindrical structure 486 is glued to the distal end of optical fiber 488. Examples of dimensions of tube 486 for a 50/55/65 micron diameter optical fiber are about 2 mm in length and between about 0.008 to 0.020 inches in diameter, with the distal optical fiber tip anchored within about 250 microns of the distal opening of cylinder 486. Delivering short duration, high frequency, low energy, pulsed radiation, as described herein, to fiber 488 causes fluid to be sucked through distal opening 490 and pumped out of proximal opening 492, creating a force that tends to pull on fiber 488. The pumping or jetting action at the distal end of fiber 480 causes the fiber to track upstream in a blood vessel, for example, as the fiber is paid out. Speeds estimated to be about 10 cm/sec were observed using a single fiber. If the device is placed downstream of an occlusion in a vessel, pulsed radiation delivered to the fiber causes the device to approach the occlusion and cause emulsification as the clot passes within the emulsification zone of the fiber.

A number of these devices can be bundled together, as shown for example in FIG. 14B. When pulsed radiation is delivered to different ones of fibers 494, directional pull on the apparatus is produced as a result of a non-central-axial force vector, created by the non-centralized longitudinal thrust of the apparatus. The direction of the pull depends on the geometry of the fibers and which fiber is fired. This force vector can be controlled to influence how the apparatus tracks across the face of an occlusion and causes emulsification of different areas of the occlusion.

FIGS. 15D and 15E are schematics of the distal end of the catheter shown in FIG. 15A (previously described) having a configuration with an active tip portion similar to that shown in FIG. 12A, but having a single "pumping" fiber 391 and three "chewing" fibers 394. Tube 389 approximately 1 mm long and inner diameter of from about 0.014–0.018 inches is glued between the distal inner walls 390 of inner diameter of from about 0.020 to 0.029 inches. Tube 389 has a 0.35 to 0.5 mm-deep notch 393 cut out of one side. The major distal portion of "pumping" fiber 391 is located between inner catheter wall 390 and outer catheter wall 384. The minor distal portion of fiber 391 passes between the joint of inner walls 387 and 390 and is secured to the outer surface of tube 389 such that its distal tip is located about 0.25 mm from the distalmost edge of tube 389, which is substantially coplanar with the distalmost catheter plane 391 a. Tubular portion 387 (e.g., of low density polyethylene) is glued on the distal ends of wall 390, so that its distal edge is flush with the distal edge of tube 389. Marker band 386 is added to facilitate visualization of the apparatus inside the body during use. The overall distal diameter of the construction is about 1 mm or 3French.

Side slot 397 is formed by skiving both the inner and outer walls of the catheter, and serves to eject from the apparatus fluid and emulsified material pumped in through tube 389 as a result of the action of fiber 391. The slot, typically of 3 to 10 mm long, may begin anywhere from 1 to 10 mm from the distal tip of the catheter. As the distance between the distal tip of the catheter (and thus of the fiber 391) and the slot increases, however, less pump head exists to eject pumped fluid and emulsified material. More than one slot may be used, as desired. Minimizing the spacing between fiber 391, tube 389 and tube 387 can improve the pumping performance of fiber 391.

Fibers 394 can be positioned approximately flush with the distal tip of the catheter construction, and thus may not contribute to the pumping action. Instead of being secured with a glue plug as shown in FIG. 15A, however, fibers 394 are anchored to the side wall of either portion 387 or 390 using a small patch of glue 395. Thus, if fibers 394 are positioned such that they both emulsify and create a sucking force, particulates sucked into the apparatus by fibers 394 can travel between the inner and outer walls and ejected through side slot 397. Alternatively, the emulsified particulates might potentially be trapped between the walls and withdrawn from the patient after recanalization.

Although only one pumping fiber and three chewing fibers are disclosed in this embodiment, other combinations of fibers are possible. Radiation pulses are distributed between the various fibers as desired. Two examples would be to evenly distribute groups of three pulses of energy with a 0.33 duty cycle between the four fibers, so that each fiber receives 25% of the average energy delivered to the site of the occlusion. Alternatively, the average energy can be delivered evenly between the chewing and pumping fibers, so that each set of fibers receives about 50% of the energy delivered. In the fiber arrangement disclosed in FIGS. 15D and 15E, for example, a pulse train could be delivered to the single pumping fiber after every delivery to one of the three chewing fibers, so that for every pulse train received by a particular chewing fiber, the pumping fiber would receive three. Distributing radiation pulses in this manner will help to increase the continuity of the pumping and emulsification actions, and will reduce periods of inaction of the two. In addition, since the pumping fiber alone will tend to attract fluid/particles to the device, and the chewing fibers alone will tend to repel fluid/particles from the device, the pumping and chewing fibers can be controlled to address potential clogging. In other words, if the device starts to become overwhelmed with occlusive material, the pumping fiber could be turned off while leaving the chewing fibers on, so that the material would be emulsified and/or repelled to clear the unit for further pumping/disruption.

Alternatively, the device could be used to probe the vessel for the location of the clot with only the chewing fibers operating, and then based on the duration information provided by the bubble feedback system (bubble duration being less for clot than for blood), the pumping fiber could be turned on once the device reached the vicinity of the clot. In other words, just as was described in the previous patent applications that have been herein incorporated by reference, the pumper and/or the chewer fibers could be controlled using bubble feedback information to avoid inefficiently introducing heat into the system.

FIGS. 16A and 16B depict an alternative construction to that shown in FIGS. 15D and 15E for a similar fiber arrangement. Nozzle 371 may be a solid piece of polyether block amide (such as PEBAX 7233, made by AtoChem)) with Shore D hardness of about 70, or some other similar, suitable polymeric material. Nozzle 371 is extruded as a tube with inner diameter equal to the widest portion of the final nozzle construction, and with multiple lumens 369 created within the walls of the PEBAX construction. Because of this construction, the PEBAX cannot be too soft, otherwise the lumens cannot hold their form and collapse. These lumens ultimately will house optical fibers 391 and 394. The nozzle is created by gently heating the PEBAX material and collapsing it around a mandrel with an outside diameter equal to the desired inner diameter of the distal portion of the nozzle. Typical dimensions of the nozzle to fit a 3French, 1-mm OD catheter are 0.022 inches proximal inner diameter to 0.018 inches distal inner diameter, about 2 mm in length, with a 1 mm long necked portion. Nozzle 371 is secured to the inner wall of the catheter with cyanoacrylate glue. "Pumper" fiber 391, present between inner and outer catheter walls as previously described, is positioned in one of the lumens 369 of nozzle 371 and terminates about 250 microns from the distal plane of the apparatus such that it creates a pumping motion as described herein that results from pulsed radiation energy. The removed portion 375 of nozzle 371 permits the fiber tip 373 of "pumping" fiber 391 to extend slightly into the inlet port 379. Each of "chewing" fibers 394 is positioned in the pattern shown, for example, inside another lumen 369 in nozzle 371 flush with the distal plane of the apparatus. These fibers act to emulsify occlusive material before such is drawn in through distal port 379 and ejected through side slot 397.

Although side slot 297, as shown, consists of two skives, one in each of the inner and outer wall of the catheter about 1 cm back from the apparatus' distal plane, the side slot may also comprise a series of smaller holes in either or both of the inner and outer walls. Replacing a skive in the inner wall, for example, with three smaller holes increases the strength of the apparatus and may prevent collapse of that portion of the device as it is pushed through a body lumen towards the site of an occlusion. In addition, a fiber (not shown) can be positioned in the vicinity of the skives or smaller exit port holes, so that acoustic phenomena generated by that fiber can help to force material out of the exit port(s) and to prevent clogging in the exit port region.

An alternate set of "chewing" fibers is also shown in FIGS. 16A and 16B. Fibers 377 could be used instead of, or in addition to, fibers 394. Since fibers 377 have the last 1 mm or so of their distal tips free, they may have the advantage of fibers 394 of being able to better emulsify occlusive material, since it is believed that free tips contribute to better emulsification. Fibers 377 could be positioned by feeding the fiber from in between the inner and outer catheter walls into a lumen 369 of nozzle 371, and then out of a slit in the outer wall of nozzle 371 (at which point it is glued) so that the distal fiber tip is approximately flush with the distal plane of the apparatus.

Marker band is shown in FIGS. 16A and 16B as mounted on the nozzle rather than on the outermost tubular material, another possible location. The inner location as shown provides the advantage of streamlining the distal outer diameter of the apparatus.

FIG. 17 shows another embodiment of the present invention. This particular embodiment further illustrates that the current invention can be used to mechanically disrupt occlusive material wholly apart from any emulsification action. Fiber 514 creates the pumping action through distal port 526. Instead of being flush with the distal catheter plane, as in previous embodiments, outer catheter wall 528 extends beyond inner catheter wall 524 by about 100 to 250 microns, for example, and is sliced as shown to form flaps 518. Flaps 518 will be long enough so that the bubbles formed by the chewing fibers will be approximately centered on the flaps, to generate sufficiently-levered force. For the dimensions of the present example, flaps 518 might be 500 microns or more in length, roughly centered on the distal tips of fibers 516, so that the distal edge of a flap extends about 250 microns past distal plane 530, with one or two flaps per fiber for a 200–400 micron diameter catheter tip. When fibers 516 (nine shown for illustrative purposes) are fired in conjunction with the pumping action of fiber 514, flaps 518 vibrate. Holding this distal tip of the catheter gently against a mass of occlusive material can cause the vibrating flaps slowly to abrade and disrupt the surface of the occlusive material. The user should be careful not to overwhelm this capability by forcing the distal tip into the occlusion, which causes damping and thus renders less effective the vibrating flaps. Typical materials of construction and dimensions for this embodiment are as described herein.

FIG. 17 also illustrates an alternative method of mounting the pumping fiber 514. Tube 520, for example, may comprise polyimide tubing with a nominal major length of about 1-mm, with portion 522 removed leaving a minor length of about 0.5-mm. Fiber 514 is glued to the outside of tube 520 as shown so that the distal end extends about 250 microns past the lowest point of tube 520, as shown. Tube 520 is glued to the inside of the inner walls 524 of the distal tip of a catheter. Fibers 516 are secured between inner catheter wall 524 and outer wall 528. Although fiber 514 is shown passing down the inner lumen of the catheter shown in FIG. 17, fiber 514 can be positioned as shown in FIG. 15D, such that only the minor distal portion is positioned in the inner lumen secured to tube 520, with the remaining portion of the fiber also located between the catheter's inner and outer walls. This could be accomplished, for example, by creating a small slit in the inner wall 524 and passing the fiber from between the inner and outer catheter walls through the slit and into the inner lumen where it could be secured to tube 520. If such a construction were used in the embodiment shown in FIGS. 15D and 15E, the distal tip of fiber 514 would still be positioned about 250 microns from the distal plane of the catheter, for example, such that delivery of short duration, high frequency, low energy pulses of radiation created the pumping phenomenon described herein. In the embodiment shown in FIG. 17, the distal tip of fiber 514 is positioned about 250 microns from the distal plane 530.

FIG. 18 depicts another embodiment within the scope of the present invention that relies on the pumping phenomenon created by the repetitive expansion and collapse of bubbles to activate a piston-like devices for attacking and breaking-up occlusive material. Optical fiber 500 is positioned relative to side hole 502 such that as short-duration, high frequency, low energy, pulsed radiation is delivered to the optical fiber, ambient fluid is pumped through inlet port 502 and into internal sealed cavity 508. As hood 510 moves away from the fiber distal tip towards the occlusion as a result of the fluid intake and the bubble formation, port 502 seals. As hood 510 reaches its most remote position, port 506 opens to the vessel as a result of hole 504 aligning with port 506. As the hood 510 tends to return to its original position to begin another cycle, the extra fluid due to heat-induced expansion escapes through port 506 due to the compressive force caused by the elasticity of the hood. This return force can be aided by attaching a spring (not shown) to hood 510. Nubs 512 repetitively tear into the occlusion as the device pulsates.

In connection with the desire to avoid unnecessary heating at the distal tip of the catheter, described briefly herein and in the patent applications incorporated by reference, any of the preceding embodiments may include a thermocouple to monitor the temperature of the site of the occlusion during operation of the invention. Said thermocouple may, for example, be positioned between the inner and outer catheter walls and flush with the distal tip or at another location between the inlet and outlet ports, and could be used to trigger an audio or a visual alarm or to control the laser to avoid further heating of the operation site once the temperature of the distal tip exceeds, for example, 50 degrees Centigrade.

While the foregoing has described preferred illustrative embodiments of the invention, other embodiments of the invention would be obvious to one of ordinary skill in the art and are encompassed by the following claims, which are of broader scope than the specific embodiments disclosed. Moreover, while the context in which the current invention has been explained concerns addressing a total or partial occlusion of a human vessel, the present invention, including its pumping/sucking aspects, would have application beyond the human body to any context in which it would be practical to move fluid from one location to another using radiation energy. Furthermore, while certain materials of construction have been identified herein, the inventions are not particularly dependent upon the types of materials used. Finally, it may be possible to achieve some or all of the phenomena described in the present disclosure by using forms of radiation other than pulsed radiation, such as continuous wave radiation. The disclosure of pulsed radiation herein should not be understood as limiting the scope of the present invention.

We claim:

1. A method of pumping fluid, comprising:

providing a flow channel in a source of fluid external thereto; and delivering radiation energy to fluid within said flow channel such that at least one transitory bubble is formed therein, said delivering sufficient to cause a portion of fluid external to the flow channel to move via said flow channel.

2. The method of claim 1, wherein said radiation energy comprises a plurality of pulses of radiation energy, said delivering such that a plurality of transitory bubbles forms in fluid within said flow channel.

3. The method of claim 1, wherein said flow channel comprises an inlet port and fluid external to said flow channel is moved through said inlet port.

4. The method of claim 1 or 2, said delivering such that fluid within said flow channel directly absorbs said radiation energy to form said transitory bubble.

5. The method of claim 1 or 2, said delivering such that fluid external to said flow channel moves via an expansion and a collapse of said bubble.

6. A method of pumping fluid, comprising:

providing a flow channel in source of fluid, and delivering radiation energy within said flow channel such that a portion of said fluid moves from said source into said flow channel.

7. The method of claim 6, said delivering such that fluid moves via said flow channel to a location external to said flow channel.

8. The method of claim 6 or 7, said delivering such that a plurality of transitory bubbles form in fluid within said flow channel.

9. A method for treating a fluid-filled body vessel that is at least partially blocked by occlusive material, comprising:

providing a flow channel having an inlet port, said inlet port positioned in a vicinity of said occlusive material;

delivering radiation energy to said flow channel such that a plurality of transitory bubbles form in the vicinity of said occlusive material, said delivering sufficient to cause flow to develop in said flow channel through said inlet port and at least a portion of said occlusive material to be disrupted.

10. A method for treating a fluid-filled body vessel that is at least partially blocked by occlusive material, comprising:

providing a flow channel having an inlet port, said inlet port positioned in a vicinity of said occlusive material;

delivering radiation energy to the vicinity of said occlusive material such that flow develops in said channel through said inlet port and at least a portion of said occlusive material is disrupted.

11. The method of claim 2 or 6 or 9 or 10, wherein said radiation energy comprises pulses of laser energy.

* * * * *